United States Patent [19]

Okamoto et al.

[11] Patent Number: 4,687,756
[45] Date of Patent: Aug. 18, 1987

[54] VULCANIZATION ACCELERATOR, A MEANS FOR ACCELERATING VULCANIZATION AND AN IMPROVED RUBBER PRODUCT CONTAINING SAID ACCELERATOR THEREIN

[75] Inventors: Akinori Okamoto, Toyonaka; Tetsuo Yamaguchi, Hirakata; Haruki Okamura, Osaka; Eizo Okino, Kurashiki, all of Japan

[73] Assignee: Sumitomo Chemical Company, Limited, Osaka, Japan

[21] Appl. No.: 800,703

[22] Filed: Nov. 22, 1985

[30] Foreign Application Priority Data

Dec. 3, 1984 [JP] Japan .................................. 59-255955

[51] Int. Cl.$^4$ ............................................. B01J 31/02
[52] U.S. Cl. .................................... 502/165; 502/167; 525/348; 544/359; 428/395
[58] Field of Search ................ 502/167, 165; 525/348; 544/359

[56] References Cited

U.S. PATENT DOCUMENTS

| | | | |
|---|---|---|---|
| 3,343,582 | 9/1967 | Himes et al. ..................... | 502/167 X |
| 3,644,304 | 2/1972 | Bearens ............................ | 525/348 X |
| 4,110,319 | 8/1978 | Lawrence .......................... | 525/348 |
| 4,224,200 | 9/1980 | Lamb ............................... | 502/167 X |

*Primary Examiner*—Patrick P. Garvin
*Attorney, Agent, or Firm*—Stevens, Davis, Miller & Mosher

[57] ABSTRACT

A vulcanization accelerator containing as an active ingredient a compound having at least one dithiocarbamoyl group, which is shown by the following general formula [I], a means for accelerating vulcanization by adding said compound and rubber products having improved quality which is attained by using said compound as a vulcanization accelerator:

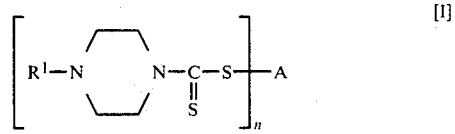

wherein $R^1$ stands for an alkyl group having one to 12 carbon atoms, a cycloalkyl group having 3 to 8 carbon atoms, an aryl group having 6 to 12 carbon atoms or an aralkyl group having 7 to 13 carbon atoms, A stands for a group shown by the formula

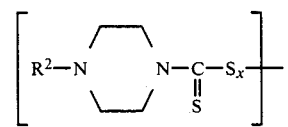

or metallic atom; in which x represents zero or an integer of 1 to 5, $R^2$ is an alkyl group having one to 12 carbon atoms, a cycloalkyl group having 3 to 8 carbon atoms, an aryl group having 6 to 12 carbon atoms or an aralkyl group having 7 to 13 carbon atoms; and n is one when A stands for a group shown by the formula

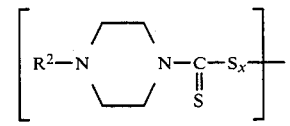

and is an integer of 1 to 4 corresponding to the valency when A stands for a metallic atom.

4 Claims, No Drawings

VULCANIZATION ACCELERATOR, A MEANS FOR ACCELERATING VULCANIZATION AND AN IMPROVED RUBBER PRODUCT CONTAINING SAID ACCELERATOR THEREIN

BACKGROUND OF THE INVENTION

1. Field of the Invention

This invention relates to a vulcanizing accelerator, more particularly a vulcanization accelerator having no adverse effect on polyester fibre used as a reinforcing agent for rubber.

2. Description of the Prior Art

In rubber products such as tires, belts, hoses and the like, fibres such as polyester, nylon, rayon and the like have heretofore been used as reinforcing materials. Among them, polyester resins have a high modulus of elasticity and an excellent dimentional stability, therefore in recent years, the demand for rubber products using polyester fibers has increased.

In vulcanizing a rubber, in particular, a lower unsaturated rubber having a small number of double bonds such as isobutylene-isoprene rubber or the like by using polyester fiber, there has heretofore been generally used a method using as a vulcanization accelerator a thiuram derivative such as tetramethylthiuram disulfide, tetraethylthiuram disulfide, tetramethylthiuram monosulfide or the like because it is advantageous, for example, in that the vulcanization rate is rapid and that the vulcanization density of the product obtained is high.

However, although the conventional thiuram type vulcanization accelerators have such advantages, they have a great disadvantage in that they deteriorate polyester fibres and lower their strength, and they have been strongly desired to be improved in this point (Journal of The Society of Rubber Industry, Japan, Vol. 54, No. 2, p. 123).

SUMMARY OF THE INVENTION

In order to solve such problems, the present inventors have devoted themselves to research on vulcanization accelerators, and have consequently found that when a compound having a specific dithiocarbamoyl group is used, it hardly deteriorates polyester fibers, is by no means inferior to well-known vulcanization accelerators in vulcanization rate and in the vulcanization density of the resulting vulcanized rubber, and is hence sufficiently satisfactory, whereby this invention has been accomplished.

That is to say, an object of this invention is to provide a very excellent vulcanization accelerator containing as an active ingredient an N-substituted piperazyldithiocarbamoyl derivative shown by the general formula [I]:

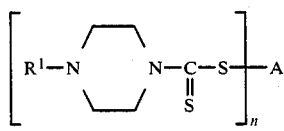

wherein $R^1$ stands for an alkyl group having one to 12 carbon atoms, a cycloalkyl group having 3 to 8 carbon atoms, an aryl group having 6 to 12 carbon atoms or an aralkyl group having 7 to 13 carbon atoms, A stands for a group shown by the formula

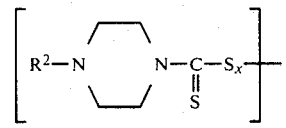

or metallic atom; in which x represents zero or an integer of 1 to 5, $R^2$ is an alkyl group having one to 12 carbon atoms, a cycloalkyl group having 3 to 8 carbon atoms, an aryl group having 6 to 12 carbon atoms or an aralkyl group having 7 to 13 carbon atoms; and n is one when A stands for a group shown by the formula

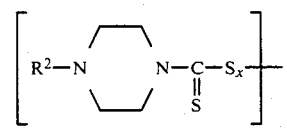

and is an integer of 1 to 4 corresponding to the valency when A stands for a metallic atom.

Another object of this invention is to provide a means for accelerating vulcanization which comprises adding to a rubber an N-substituted piperazyldithiocarbamoyl derivative shown by the above general formula I.

Further another object of this invention is to provide an excellent rubber product by accelerating vulcanization by addition of the aforesaid compound with almost no deterioration of polyester fibers used together with rubber in tires and the like.

Such an N-substituted piperazyldithiocarbamoyl derivative can easily be produced by a well-known process, for example, the following process. One which is produced by a process other than said process, of course, is also employable in this invention.

An N-substituted piperazylthiuram derivative which is used for one of the embodiments of this invention can easily be produced by the well-known process described below.

A sodium dithiocarbamate derivative is produced by reacting N-substituted piperazine with carbon disulfide in the presence of sodium hydroxide. Subsequently, the sodium dithiocarbamate derivative is oxidized, whereby the corresponding thiuram disulfide is produced. Then, said disulfide is reacted with potassium cyanide or the like, whereby the corresponding thiuram monosulfide can be produced. By reacting the aforesaid sodium dithiocarbamate derivative with sulfur monochloride, the corresponding thiuram polysulfide can also be produced.

The metal N-substituted piperazyldithiocarbamate which is used for another embodiment of this invention can easily be produced by the following process.

A sodium dithiocarbamate derivative which is an intermediate is produced by reacting N-substituted piperazine with carbon disulfide in the presence of sodium hydroxide. Subsequently, the reaction solution is reacted with an aqueous solution containing a metallic ion such as, for example, an aqueous zinc sulfate solution, whereby the corresponding dithiocarbamic acid of metal salt such zinc dithiocarbamate can be produced.

DESCRIPTION OF THE PREFERRED EMBODIMENTS

The compound [I] having at least one N-substituted piperazyldithiocarbamoyl group used in this invention includes, for example, thiuram monosulfides, thiuram disulfides, thiuram polysulfides and metal dithiocarbamates all obtained by using, as starting materials, N-substituted piperazine derivatives, for example, N-alkylpiperazines which are substituted on the nitrogen by an alkyl group such as methyl, ethyl, n-propyl, i-propyl, n-butyl, i-butyl, sec-butyl, tert-butyl, pentyl, amyl, hexyl, heptyl, octyl, nonyl, decyl, undecyl, dodecyl or the like; N-cycloalkylpiperazines which are substituted on the nitrogen by a cyclopropyl, cyclopentyl, cyclohexyl, cycloheptyl, cyclooctyl group or the like; and N-substituted piperazines which are substituted on the nitrogen by an aryl or aralkyl group such as phenyl, methylphenyl, ethylphenyl, propylphenyl, naphthyl, methylnaphthyl, benzyl, phenylethyl or the like. Among them, thiuram derivatives or metal dithiocarbamates obtained by using N-methylpiperazine as a starting material are preferred.

The vulcanization accelerator of this invention contains as an active ingredient a compound having at least one N-substituted dithiocarbamoyl group which is shown by the above general formula [I] and such a compound shown by the general formula [I] may be used alone or in combination with guanidine derivatives such as diphenyl guanidine, ditolylguanidine and the like; thiazole derivatives such as mercaptobenzothiazole, dibenzothiazyl disulfide and the like; and/or sulfenamide derivatives such as N-cyclohexylbenzothiazylsulfenamide, N-t-butylbenzothiazylsulfenamide, N-oxydiethylenebenzothiazylsulfenamide and the like. In particular, simultaneous use of the compound shown by the general formula [I] and the guanidine derivatives and/or thiazole derivatives is preferred because it yields a vulcanized rubber having high tensile stress and tensile strength. In using them together with the compound shown by the general formula [I], they may be either used in the form of a mixture prepared by previously mixing them with said compound, or mixed therewith at the time of use.

Although the vulcanization accelerator of this invention is usually used in lower unsaturated rubbers such as isobutylene-isoprene rubber (IIR), ethylene-propylenediene rubber (EPDM) and the like, it can be used also in natural rubber (NR), styrene-butadiene rubber (SBR), isoprene rubber (IR), butadiene rubber (BR), chloroprene rubber (CR), acrylonitrile-butadiene rubber (NBR), etc. As to the amount of said vulcanization accelerator added to rubber, the vulcanization accelerator is used usually in an amount in the range from 0.1 to 10 parts by weight per 100 parts by weight of rubber.

In using the vulcanization accelerator of this invention, there may be, if necessary, used conventional additives, for example, zinc oxide, magnesium oxide, stearic acid, carbon black, silica, clay, sulfur, process oils, antioxidants, etc.

This invention is further explained in more detail referring to Examples and Referential Examples, which are not by way of limitation but by way of illustration.

REFERENTIAL EXAMPLE 1

Production example of bis(N-methylpiperazyl)thiuram disulfide

With 30 g of N-methylpiperazine were mixed 90 g of water and 43 g of sodium hydroxide, and the temperature of the resulting solution was lowered to 7° C. While maintaining the solution temperature at 7° to 10° C., 25 g of carbon disulfide was added dropwise.

A solution of 99 g of potassium ferricyanide in 400 g of water was added dropwise to the resulting solution at 5° to 10° C. over a period of 1 hour. The deposited crystals were separated by filtration, and washed with water. There was obtained 48.7 g of white powder: yield 92.6%, m.p. 148°–149° C.

Elementary analysis values for bis(N-methylpiperazyl)thiuram disulfide:

| $C_{12}H_{22}N_4S_4$ | C | H | N | S |
|---|---|---|---|---|
| Calculated: | 41.11 | 6.33 | 15.98 | 36.58 |
| Found: | 41.20 | 6.25 | 15.85 | 36.62. |

REFERENTIAL EXAMPLE 2

Production example of bis(N-phenylpiperazyl)thiuram disulfide

With 49 g of N-phenylpiperazine were mixed 90 g of water and 43 g of sodium hydroxide, and the temperature of the resulting solution was lowered to 7° C. While maintaining the solution temperature at 7° to 10° C., 25 g of carbon disulfide was added dropwise.

A solution of 99 g of potassium ferricyanide in 400 g of water was added dropwise to the resulting solution at 5° to 10° C. over a period of 1 hour. The deposited crystals were separated by filtration, and washed with water. There was obtained 64.9 g of white powder: yield 91.0%.

Elementary analysis values for bis(N-phenylpiperazyl)thiuram disulfide:

| $C_{22}H_{26}N_4S_4$ | C | H | N | S |
|---|---|---|---|---|
| Calculated: | 55.70 | 5.49 | 11.81 | 27.00 |
| Found: | 55.83 | 5.38 | 11.76 | 27.03. |

REFERENTIAL EXAMPLE 3

Production example of zinc N-methylpiperazyldithiocarbamate

With 20 g of N-methylpiperazine were mixed 80 g of water and 8 g of sodium hydroxide, and the temperature of the resulting solution was lowered to 7° C. While maintaining the solution temperature at 7° to 10° C., 17 g of carbon disulfide was added dropwise.

A solution of 19 g of zinc sulfate in 100 ml of water was added dropwise to the resulting solution while maintaining the temperature of the latter solution at 30° to 35° C. The deposited crystals were separated by filtration, and washed with water. There was obtained 39.5 g of white powder: yield 95.0%, m.p. 254°–256° C.

Elementary analysis values for zinc N-methylpiperazyldithiocarbamate:

| $C_{12}H_{22}N_4S_4Zn$ | C | H | N | S | Zn |
|---|---|---|---|---|---|
| Calculated: | 34.64 | 5.34 | 13.47 | 30.83 | 15.72 |
| Found: | 34.59 | 5.32 | 13.49 | 30.90 | 15.60. |

In the same manner as described above, there can be obtained the following compounds:
nickel N—methylpiperazyldithiocarbamate,
copper N—methylpiperazyldithiocarbamate,
cadmium N—methylpiperazyldithiocarbamate,
iron N—methylpiperazyldithiocarbamate,
cobalt N—methylpiperazyldithiocarbamate, and
mercury N—methylpiperazyldithiocarbamate.

Some physical properties of the N-methylpiperazine derivatives described above are shown in Table 1.

TABLE 1
Some Physical Properties of Thus Obtained Compounds

| Compound | Colour | m.p. (°C.) |
|---|---|---|
| Nickel N—methylpiperazyldithiocarbamate | Green | 287–289 |
| Copper N—methylpiperazyldithiocarbamate | Brown | 272–274 |
| Cadmium N—methylpiperazyldithiocarbamate | White | 278–280 |
| Iron N—methylpiperazyldithiocarbamate | Dark brown | 243–245 |
| Cobalt N—methylpiperazyldithiocarbamate | Green | 303–305 |
| Mercury N—methylpiperazyldithiocarbamate | Pale yellow | 223–225 |

PREFERENTIAL EXAMPLE 4

Production example of copper N-phenylpiperazyldithiocarbamate

With 32 g of N-phenylpiperazine were mixed 90 g of water and 8 g of sodium hydroxide, and the temperature of the resulting solution was lowered to 7° C. While maintaining the solution temperature at 7° to 10° C., 17 g of carbon disulfide was added dropwise.

A solution of 18 g of cupric sulfate in 100 ml of water was added dropwise to the resulting solution while maintaining the temperature of the latter solution at 30° to 35° C. The deposited crystals were separated by filtration, and washed with water. There was obtained 50.0 g of light brown powder: yield 94.2%. This product decomposed at 200° C. or higher.

Elementary analysis values for copper N-phenylpiperazyldithiocarbamate:

| $C_{22}H_{26}N_4S_4Cu$ | C | H | N | S | Cu |
|---|---|---|---|---|---|
| Calculated: | 49.08 | 4.88 | 10.41 | 23.82 | 11.81 |
| Found: | 49.00 | 4.92 | 10.36 | 23.91 | 11.73 |

EXAMPLE 1

A rubber composition was prepared according to the following recipe by mixing by means of an open roll in a conventional manner.

| Recipe: | |
|---|---|
| EPDM (Esprene ® 501A mfd. by Sumitomo Chemical Industries Ltd.) | 100 parts by weight |
| Stearic acid | 1 parts by weight |
| Zinc oxide | 5 parts by weight |
| HAF carbon | 200 parts by weight |
| Process oil | 75 parts by weight |
| Sulfur | 1.5 parts by weight |
| Vulcanization accelerator (listed in Table 2) | 2.5 parts by weight |

A part of the rubber composition thus obtained was used, and a 1500 d/2 polyester cord was embedded near the surface of a sheet of the rubber composition, which was them vulcanized at 150° C. at 90 kg/cm² for 40 minutes.

Subsequently, a part of the polyester cord was drawn out from the vulcanized product thus obtained, after which the vulcanized product was heat-treated at 175° C. for 2 hours. Then, the residual polyester cord was drawn out therefrom, and the strengths of the polyester cord before and after the heat treatment were measured according to JIS K-6301. The results obtained are shown in Table 3.

By use of the residual rubber composition, Mooney scorch test was carried out according to JIS K-6300, and the vulcanization properties were measured according to ASTM D-2084 and the tensile properties according to JIS-K-6301.

The results of these tests and measurements are also shown in Table 3.

TABLE 2
Vulcanization Accelerators

| No. | Vulcanization accelerator |
|---|---|
| A | Bis(N—-methylpiperazyl)thiuram disulfide/ 2-mercaptobenzothiazole = 2/0.5 |
| B | Bis(N—phenylpiperazyl)thiuram disulfide/ 2-mercaptobenzothiazole = 2/0.5 |
| C | Bis(N—cyclohexylpiperazyl)thiuram disulfide/2-mercaptobenzothiazole = 2/0.5 |
| D | Zinc N—-methylpiperazyldithiocarbamate/ 2-mercaptobenzothiazole = 2/0.5 |
| E | Copper N—phenylpiperazyldithiocarbamate/ 2-mercaptobenzothiazole = 2/0.5 |
| F (Comparative Example) | Tetramethylthiuram disulfide/ 2-mercaptobenzothiazole = 2/0.5 |

TABLE 3
Test Results

| Physical Properties | | Example | | | | | Comparative Example |
|---|---|---|---|---|---|---|---|
| | | Vulcanization accelerator | | | | | |
| | | A | B | C | D | E | F |
| Strength of cord | Before heat treatment (kg) | 23.5 | 23.5 | 23.5 | 23.5 | 23.5 | 20.4 |
| | After heat treatment (kg) | 23.0 | 22.6 | 22.1 | 21.3 | 20.5 | 3.3 |
| | Retention (%) | 98 | 96 | 94 | 91 | 87 | 16 |
| Physical properties of rubber | Mooney scorch test (140° C.) | | | | | | |
| | $t_5$ (min) | 6.8 | 6.7 | 6.6 | 4.3 | 4.5 | 6.5 |
| | $t_{\Delta 30}$ (min) | 2.3 | 2.4 | 2.6 | 1.8 | 1.9 | 2.3 |
| | Rheometer test (170° C.) | | | | | | |
| | $t_{10}$ (min) | 7.4 | 8.2 | 8.3 | 4.7 | 4.9 | 7.2 |
| | $t_{90}$ (min) | 19.0 | 20.7 | 21.1 | 15.3 | 15.7 | 18.4 |
| | $t_{90}-t_{10}$ (min) | 11.6 | 12.5 | 12.8 | 10.6 | 10.8 | 11.2 |
| | $T_{max}$ (kg · cm) | 134 | 130 | 124 | 116 | 114 | 136 |
| | Tensile properties (Vulcanization conditions = 170° C. × 40 min) | | | | | | |
| | Tensile strength (kg/cm²) | 228 | 218 | 215 | 197 | 194 | 229 |

TABLE 3-continued

| | Test Results | | | | | |
|---|---|---|---|---|---|---|
| | Example | | | | | Comparative Example |
| Physical Properties | Vulcanization accelerator | | | | | |
| | A | B | C | D | E | F |
| Elongation (%) | 590 | 600 | 610 | 510 | 500 | 590 |
| 300% Tensile stress (kg/cm$^2$) | 97 | 96 | 95 | 84 | 82 | 98 |

EXAMPLE 2

A compounded rubber was prepared according to the following recipe in the same manner as in Example 1 and tested in the same manner as in Example 1. The results obtained are shown in Table 5.

| Recipe: | |
|---|---|
| IIR (Butyl 301 mfd. by Nihon Butyl Co., Ltd.) | 100 parts by weight |
| Stearic acid | 1 parts by weight |
| Zinc oxide | 5 parts by weight |
| SRF carbon | 60 parts by weight |
| Process oil | 20 parts by weight |
| Sulfur | 2 parts by weight |
| Vulcanization accelerator | Listed in Table 4 |

EXAMPLE 3

A compounds rubber was prepared according to the following recipe in the same manner as in Example 1 and tested in the same manner as in Example 1. The results obtained are shown in Table 6.

| Recipe: | |
|---|---|
| NR (RSS #1) | 100 parts by weight |
| Zinc oxide | 5 parts by weight |
| Stearic acid | 3 parts by weight |
| Process oil | 3 parts by weight |
| HAF carbon black | 45 parts by weight |
| Sulfur | 2 parts by weight |
| Vulcanization accelerator | Listed in Table 6 |

TABLE 4

| Vulcanization Accelerators | | |
|---|---|---|
| No. | Vulcanization accelerator | Adding amount |
| G | Bis(N—methylpiperazyl) thiuram disulfide | 1 part by weight |
| H | Bis(N—methylpiperazyl) thiuram disulfide/ diphenylguanidine | 1/0.5 |
| I | Bis(N—phenylpiperazyl) thiuram disulfide | 1 |
| J | Bis(N—cyclohexylpiperazyl) thiuram disulfide | 1 |
| K | Zinc N—methylpiperazyl-dithiocarbamate | 1 |
| L | Copper N—phenylpiperazyl-dithiocarbamate | 1 |
| M (Comparative Example) | Tetramethylthiuram disulfide | 1 |

TABLE 6

| Vulcanization accelerators | | |
|---|---|---|
| No. | Vulcanization accelerator | Adding amount |
| N | Bis(N—methylpiperazyl) thiuram disulfide | 1 part by weight |
| O | Bis(N—methylpiperazyl) thiuram disulfide/ diphenylguanidine | 1/0.5 |
| P | Bis(N—methylpiperazyl) thiuram disulfide/ 2-mercaptobenzothiazole | 1/0.5 |
| Q | Bis(N—phenylpiperazyl) thiuram disulfide | 1 |
| R | Zinc N—methylpiperazyl-dithiocarbamate | 1 |
| S | Copper N—phenylpiperazyl-dithiocarbamate | 1 |
| T (Comparative Example) | Tetramethylthiuram disulfide | 1 |

TABLE 5

| | | Test Results | | | | | | |
|---|---|---|---|---|---|---|---|---|
| | | Example | | | | | | Comparative Example |
| Physical Properties | | Vulcanization accelerator | | | | | | |
| | | G | H | I | J | K | L | M |
| Strength of cord | Before heat treatment (kg) | 23.4 | 23.4 | 23.4 | 23.4 | 23.4 | 23.4 | 20.8 |
| | After heat treatment (kg) | 22.7 | 22.5 | 21.8 | 21.1 | 20.8 | 20.1 | 4.5 |
| | Retention (%) | 97 | 95 | 93 | 90 | 89 | 86 | 21.6 |
| Physical properties of rubber | Mooney scorch test (140° C.) | | | | | | | |
| | $t_5$ (min) | 12.5 | 10.4 | 14.1 | 15.7 | 7.9 | 8.3 | 12.6 |
| | $t_{\Delta 30}$ (min) | 3.9 | 3.6 | 4.54 | 5.8 | 2.6 | 2.9 | 3.9 |
| | Rheometer test (170° C.) | | | | | | | |
| | $t_{10}$ (min) | 3.9 | 3.3 | 4.4 | 5.6 | 2.5 | 2.6 | 4.0 |
| | $t_{90}$ (min) | 24.0 | 29.1 | 35.2 | 38.3 | 21.9 | 21.6 | 21.5 |
| | $t_{90}-t_{10}$ (min) | 20.1 | 25.8 | 30.8 | 37.7 | 19.4 | 19.0 | 17.4 |
| | $T_{max}$ (kg·cm) | 55.1 | 57.5 | 53.2 | 52.1 | 47.7 | 46.9 | 57.1 |

TABLE 7

| Physical properties | | Test Results | | | | | | |
|---|---|---|---|---|---|---|---|---|
| | | Example | | | | | | Comparative Example |
| | | Vulcanization Accelerator | | | | | | |
| | | N | O | P | Q | R | S | T |
| Strength of cord | Before heat treatment (kg) | 23.0 | 23.0 | 23.0 | 23.0 | 23.0 | 23.0 | 20.4 |
| | After heat treatment (kg) | 22.5 | 22.1 | 22.1 | 21.6 | 20.7 | 20.7 | 4.3 |
| | Retention (%) | 98 | 96 | 96 | 94 | 90 | 88 | 21.1 |
| Physical properties of rubber | Mooney scorch test (125° C.) | | | | | | | |
| | $t_5$ (min) | 10.2 | 7.4 | 8.3 | 9.1 | 6.7 | 6.3 | 6.8 |
| | $t_{\Delta 30}$ (min) | 4.0 | 2.6 | 3.3 | 4.1 | 3.3 | 3.5 | 1.8 |
| | Rheometer test (145° C.) | | | | | | | |
| | $t_{10}$ (min) | 9.7 | 4.5 | 5.2 | 6.3 | 6.4 | 6.0 | 3.5 |
| | $t_{90}$ (min) | 14.0 | 7.8 | 8.7 | 10.0 | 9.8 | 9.6 | 6.5 |
| | $t_{90} - t_{10}$ (min) | 4.3 | 3.3 | 3.5 | 3.7 | 3.4 | 3.6 | 3.0 |
| | $T_{max}$ (kg · cm) | 110.2 | 128.9 | 123.4 | 120.2 | 96.4 | 92.8 | 125.3 |
| | Tensile properties (Vulcanization conditions = 145° C. × 20 min) | | | | | | | |
| | Tensile strength (kg/cm$^2$) | 96 | 102 | 102 | 94 | 83 | 81 | 106 |
| | Elongation (%) | 640 | 620 | 580 | 680 | 560 | 540 | 640 |
| | 300% Tensile stress (kg/cm$^2$) | 38 | 40 | 40 | 32 | 33 | 31 | 40 |

What is claimed is:

1. A vulcanization accelerator containing as an active ingredient a compound having at least one dithiocarbamoyl group, which is shown by the general formula [I]:

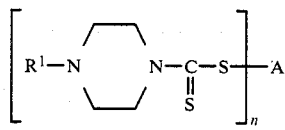

wherein R$^1$ stands for an alkyl group having one to 12 carbon atoms, a cycloalkyl group having 3 to 8 carbon atoms, an aryl group having 6 to 12 carbon atoms or an aralkyl group having 7 to 13 carbon atoms, A stands for a group shown by the formula

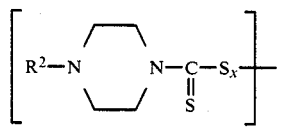

or metallic atom selected from the group consisting of zinc, copper, iron, cobalt, nickel, cadmium, and mercury; in which x represents zero or an integer of 1 to 5, R$^2$ is an alkyl group having one to 12 carbon atoms, a cycloalkyl group having 3 to 8 carbon atoms, an aryl group having 6 to 12 carbon atoms or an aralkyl group having 7 to 13 carbon atoms; and n is one when A stands for a group shown by the formula

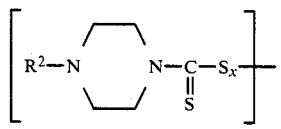

and is an integer of 1 to 4 corresponding to the valency when A stands for a metallic atom selected from the group consisting of zinc, copper, iron, cobalt, nickel, cadmium, and mercury.

2. A vulcanization accelerator according to claim 1, wherein said accelerator contains at least one compound selected from the group consisting of diphenylguanidine, ditolylguanidine, mercaptobenzothiazole, dibenzothiazyl disulfide, N-cyclohexylbenzothiazylsulfenamide, N-t-butylbenzothiazylsulfenamide, and N-oxydiethylenebenzothiazylsulfenamide.

3. A vulcanization accelerator according to claim 1, wherein said accelerator contains an anti-aging agent, zinc white, magnesium oxide, stearic acid, carbon black, silica, clay, sulfur and a process oil.

4. A vulcanization accelerator containing as an active ingredient a compound having at least one dithiocarbamoyl group, which is shown by the general formula [I]:

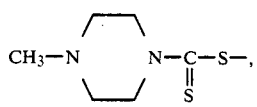

wherein R$^1$ is a group selected from the member consisting of methyl, phenyl, cyclohexyl and A is a group selected from a member consisting of

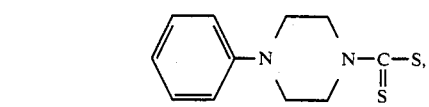

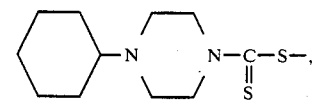

or a metallic atom selected from the group consisting of zinc, copper, iron, cobalt, nickel, cadmium and mercury.

* * * * *